United States Patent
Hyung et al.

(10) Patent No.: US 10,018,603 B2
(45) Date of Patent: Jul. 10, 2018

(54) TWO-DIMENSIONAL LIQUID CHROMATOGRAPHY SYSTEM FOR HEART-CUT METHOD

(71) Applicant: KOREA RESEARCH INSTITUTE OF STANDARDS AND SCIENCE, Daejeon (KR)

(72) Inventors: Seok-Won Hyung, Daejeon (KR); Byungjoo Kim, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 307 days.

(21) Appl. No.: 14/754,336

(22) Filed: Jun. 29, 2015

(65) Prior Publication Data
US 2016/0054273 A1    Feb. 25, 2016

(30) Foreign Application Priority Data
Aug. 20, 2014  (KR) .................. 10-2014-0108222

(51) Int. Cl.
G01N 30/46    (2006.01)
G01N 30/38    (2006.01)
G01N 30/72    (2006.01)

(52) U.S. Cl.
CPC .......... *G01N 30/463* (2013.01); *G01N 30/38* (2013.01); *G01N 30/72* (2013.01)

(58) Field of Classification Search
CPC .................................................. G01N 30/463
See application file for complete search history.

(56) References Cited

U.S. PATENT DOCUMENTS

| | | | |
|---|---|---|---|
| 7,397,388 B2* | 7/2008 | Huang | E21B 47/182 166/373 |
| 8,101,422 B2* | 1/2012 | Srinivasan | G01N 30/463 205/789 |
| 8,621,915 B2* | 1/2014 | Liu | G01N 30/463 210/656 |
| 2007/0199874 A1* | 8/2007 | Ito | G01N 30/463 210/198.2 |

FOREIGN PATENT DOCUMENTS

CN    201993351 U  *  9/2011  ............ G01N 30/08
KR    1020090058287 A    6/2009

OTHER PUBLICATIONS

Villasenor, S., "Matrix Elimination in Liquid Chromatography Using Heart-Cut Column Switching Techniques," Analytical Chemistry, vol. 63, No. 14, Jul. 1991, 5 pages.

* cited by examiner

*Primary Examiner* — John Fitzgerald
(74) *Attorney, Agent, or Firm* — McCoy Russell LLP

(57) ABSTRACT

Provided is a two-dimensional liquid chromatography system, and more particularly, a two-dimensional liquid chromatography system capable of performing both independent one-dimensional separation through a reversed-phase or normal-phase chromatography method and two-dimensional separation for removing a matrix effect in a single system.

6 Claims, 4 Drawing Sheets

TWO-DIMENSIONAL LIQUID CHROMATOGRAPHY SYSTEM FOR HEART-CUT METHOD

CROSS-REFERENCE TO RELATED APPLICATIONS

This application claims priority under 35 U.S.C. § 119 to Korean Patent Application No. 10-2014-0108222, filed on Aug. 20, 2014, in the Korean Intellectual Property Office, the disclosure of which is incorporated herein by reference in its entirety.

TECHNICAL FIELD

The following disclosure relates to a two-dimensional liquid chromatography system, and more particularly, to a two-dimensional liquid chromatography system capable of performing both independent one-dimensional separation through a reversed-phase or normal-phase chromatography method and two-dimensional separation for removing a matrix effect in a single system.

BACKGROUND

Liquid chromatography, which is a method of separating materials in a sample by interaction between a mobile-phase (eluent) and a stationary-phase, has an advantage that various materials may be simultaneously separated by one-time injection of the sample.

Meanwhile, as a method for improving efficiency of analysis, there is a two-dimensional analysis method.

On-line multi-dimensional chromatography has been used to analyze a complicated sample. In some cases, this approach is referred to as column switching. According to a column switching method, a sample is divided into multiple fractions of treatable parts and additionally analyzed.

In the case of a two-dimensional approach, unwanted materials in a sample may be delivered into waste, and additional separation is performed by flowing an analyte, which is a target of interest, to a second column.

In the prior art document, various two-dimensional separation methods have been disclosed. For example, Steven R. Villasenor (Anal. Chem., 63, (1991), 1362-1366) disclosed a matrix removing technique using a heart-cut and column switching method for analyzing sulfite in an analgesic formulation.

As another technique associated with the two-dimensional separation method, an ultrahigh-pressure cation exchanger dual on-line solid-phase extraction/capillary reverse-phase liquid chromatography system capable of maximizing analysis efficiency of a complicated bio-sample and particularly minimizing a dead time by using a two-dimensional liquid chromatography system in which a strong cation exchange chromatography and a reverse-phase liquid chromatography are on-line connected to each other has been disclosed in Korean Patent Laid-Open Publication No. 2009-0058287 (Title: Ultrahigh-pressure cation exchanger dual on-line solid-phase extraction/capillary reverse-phase liquid chromatography system, Laid-Open Publication Date: Jun. 9, 2009).

As described above, a multi-dimensional chromatography technology has been developed up to now, but in view of removing a matrix effect, there is still limitation in selectively analyzing only a material of interest. Here, the matrix may be defined as follows. At the time of analyzing a specific material contained in an arbitrary sample all materials except for the material of interest may be collectively referred to as the matrix. At the time of analyzing the materials in the sample particularly using a liquid chromatography/mass spectrometry (LC/MS), in the case in which the matrix as described above has the same elution time as that of the material of interest, the matrix affects sensitivity of a mass spectrometer, such that it is difficult to obtain an accurate measurement result. This phenomenon is referred to as a matrix effect. Therefore, a technology for removing the matrix effect with relation thereto should be continuously developed.

RELATED ART DOCUMENT

Patent Document

Korean Patent Laid-Open Publication No. 2009-0058287 (Title: Ultrahigh-pressure cation exchanger dual on-line solid-phase extraction/capillary reverse-phase liquid chromatography system, Laid-Open Publication Date: Jun. 9, 2009)

SUMMARY

An embodiment of the present invention is directed to providing a two-dimensional liquid chromatography system capable of performing both independent one-dimensional separation through a reversed-phase or normal-phase chromatography method and two-dimensional separation for removing a matrix effect in a single system. Independence as described above may be further efficient in the case of applying a heart-cut method for removing the matrix effect particularly in a two-dimensional chromatography method, and since it is possible to know accurate information on an elution time of a material separated in a first column, separation accuracy in re-separating a material of interest to a second column may be increased.

Another embodiment of the present invention is directed to providing a two-dimensional liquid chromatography system applying a dilution method in order to solve a problem of collection stability that may be generated by an eluent during a process in which a material of interest separated in a first column is eluted together with the eluent such as water or an organic solvent to thereby be collected in a second column.

Another embodiment of the present invention is directed to providing a two-dimensional liquid chromatography system capable of inducing flows of all fluids flowing through a second column so that whether or not a sample is lost may be confirmed by a mass spectrometer while the sample is collected.

In one general aspect, a two-dimensional liquid chromatography system is characterized in that in a reversed-phase or normal-phase two-dimensional liquid chromatography system 1, a first switching valve 300 and a second switching valve 400 are switched so that among materials separated in a first column, only a material of interest and a matrix having the same elution time as that of the material of interest are selectively re-separated in a second column by an eluent flowed by a first mobile-phase pump, but after the material of interest reaching the second column 600 is diluted by a diluting mobile phase supplied through a second mobile-phase pump 302 connected to the first switching valve 300 to thereby be collected, the material of interest and the matrix are separated from each other by the eluent supplied from the second mobile-phase pump again to thereby be analyzed in a mass spectrometer (MS).

The two-dimensional liquid chromatography system may include: a first column 200 primarily separating materials in an injected sample; a first switching valve 300 adjusting the materials separated in the first column 200 so as to be introduced through a second inlet port 310 and then discharged to the outside through a first drain port 301 or discharged through a second outlet port 320 and including a mobile-phase inlet port 330 connected to a second mobile-phase pump 302 so that a diluting mobile phase is introduced therethrough, and a mobile-phase outlet port 340 through which the diluting mobile phase is discharged; a second switching valve 400 adjusting the materials discharged to the second outlet port 320 so as to be directly moved to the mass spectrometer (MS) or discharged to a third outlet port 410; a T shaped connector tube 500 including a first port 510 connected to the mobile-phase outlet port 340 of the first switching valve 300, a second port 520 connected to the third outlet port 410 of the second switching valve 400, and a third port 530 in which fluids introduced through the first port 510 and the second port 520 are mixed with each other to thereby flow; and a second column 600 connected to the third port 530, secondarily separating a predetermined materials in the sample, and connected to the second switching valve 400 so that the separated material is moved to the mass spectrometer (MS) through the second switching valve 400.

In addition, the first switching valve 300 may change a flow path by a switching operation so that materials separated in the first column 200 are moved to the second switching valve 400, but may adjust whether the diluting mobile phase supplied from the second mobile-phase pump 302 passes through the second switching valve 400 to flow to the second port 520 of the T shaped connector tube 500 or is directly connected to the first port 510 through the mobile-phase outlet port 340.

Further, the second switching valve 400 may change a flow path by a switching operation so that among the materials separated in the first column 200, only a predetermined material passes through the second column 600, but adjust whether the diluting mobile phase supplied from the second mobile-phase pump 302 passes through the second column 600 to flow to the mass spectrometer (MS) or passes through the second column 600 to thereby be discharged to the outside through the second drain port 401.

A two-dimensional liquid chromatography method using the above-mentioned two-dimensional liquid chromatography system 1 includes: a) a first step of primarily separating an injected sample in the first column 200 and introducing the primarily separated sample into the mass spectrometer (MS) sequentially through the first switching valve 300 and the second switching valve 400 (S100); b) a second step of confirming elution times of materials in the sample through the first step (S100) (S200); c) a third step of discharging the other materials except for material of interest among the materials separated in the first column to the first drain port 301 by switching the first switching valve 300 (S300); and d) a fourth step of collecting material of interest among materials separated in the first column in the second column 600 through the second switching valve 400 and the T shaped connector tube 500 by switching the first switching valve 300 (S400).

Further, in the fourth step (S400), the diluting mobile phase may be discharged to the mobile-phase outlet port 340 to thereby be introduced into the first port 510 of the T shaped connector tube 500, and the material of interest introduced into the second port 520 may reach the second column 600 in a state in which the material of interest is mixed with the diluting mobile phase to thereby be diluted to a predetermined concentration.

In addition, the two-dimensional liquid chromatography method may further include, after performing the fourth step (S400) for a predetermined time, a fifth step of discharging the other materials except for the material of interest among the materials separated in the first column 200 to the first drain port 301 and introducing the material of interest into the second port 520 of the T shaped connector tube 500 through the first switching valve 300 and the second valve 400 to collect the material of interest in one end of the second column 600 together with the diluting mobile phase supplied from the second mobile-phase pump 302 by switching the first switching valve 300, and introducing the material of interest into the mass spectrometer (MS) through the eluent supplied from the second mobile-phase pump 302 after separating the material of interest in the second column 600 (S500).

DETAILED DESCRIPTION OF MAIN ELEMENTS

Figure 1:
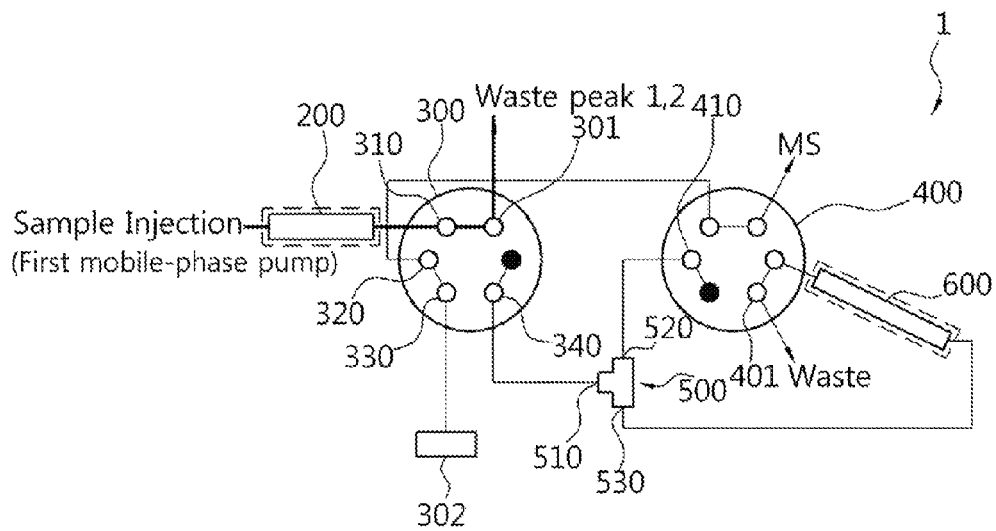
FIG. 1 is a configuration diagram illustrating a two-dimensional liquid chromatography system according to the present invention.

1: two-dimensional liquid chromatography system
MS: mass spectrometer
100: sample inlet valve
110: first inlet port
121: first connection port             122: second connection port
130: first outlet port
200: first column
300: first switching valve
301: first drain port                  302: second mobile-phase pump
310: second inlet port                 320: second outlet port
330: mobile-phase inlet port           340: mobile-phase outlet port
400: second switching valve
401: second drain port
410: third outlet port
500: T shaped connector tube
510: first port                        520: second port
530: third port
600: second column
S100~S500: each step of two-dimensional liquid chromatography method according to the present invention

DETAILED DESCRIPTION OF EMBODIMENTS

Hereinafter, a two-dimensional liquid chromatography system according to the present invention as described above will be described in detail with reference to the accompanying drawings.

The two-dimensional liquid chromatography system according to the present invention is characterized in that both independent one-dimensional separation through a reversed-phase or normal-phase chromatography method and two-dimensional separation for removing a matrix effect may be performed in a single system.

In more detail, the two-dimensional liquid chromatography system 1 according to the present invention is characterized in that a first switching valve 300 and a second switching valve 400 are switched so that among materials separated in a first column, only a material of interest is selectively re-separated in a second column, but the material of interest reaching the second column 600 is separated by an eluent supplied through a second mobile-phase pump 302 connected to the first switching valve 300 to thereby be analyzed in a mass spectrometer (MS).

First, a configuration of the two-dimensional liquid chromatography system 1 according to the present invention will be described. The two-dimensional liquid chromatography system 1 according to the present invention may roughly include a first column 200, the first switching valve 300, the second switching valve 400, a T shaped connector tube 500, and the second column 600.

Figure 2:
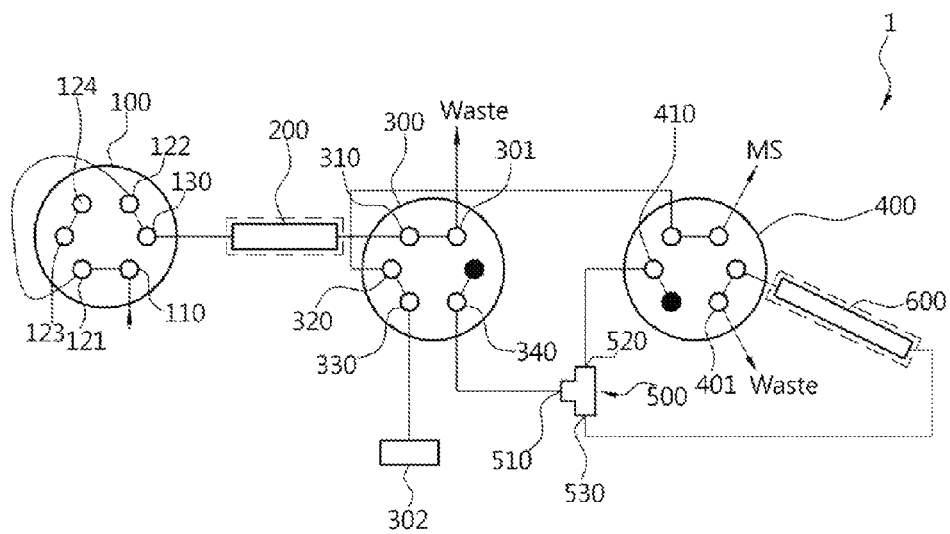
FIG. 2 is a configuration diagram illustrating a two-dimensional liquid chromatography system according to an exemplary embodiment of the present invention.

In this case, in the two-dimensional liquid chromatography system 1 according to the present invention 1, as illustrated in FIG. 2, as a unit for injecting a sample into the first column 200, a sample inlet valve 100 and a first mobile-phase pump (not illustrated) may be connected to each other.

The first mobile-phase pump (not illustrated) serves to inject the sample into the first column 200 and supply the eluent so that materials may be separated in the first column 200.

The sample inlet valve 100 includes a first inlet port 110 into which the eluent is introduced and a first outlet port 130 in which the eluent and the sample are discharged through a first connection port 121 and a second connection port 122.

In the sample inlet valve 100, the first connection port 121 may simultaneously be connected to the second connection port 122 and a third connection port 123. Alternatively, the first connection port 121 may simultaneously be connected to the first inlet port 110 and the second connection port 122.

The second connection port 122 may be in fluid-communication with a fourth connection port 124 or the first outlet port 130.

During a process in which the sample is injected through any one of the third connection port 123 and the fourth connection port 124, excess of the sample is discarded through the other port.

In this case, when the sample is filled in a sample loop connected between the first connection port 121 and the second connection port 122, the sample inlet valve 100 is switched, such that the sample sequentially passes through the first inlet port 110, the first connection port 121, the second connection port 122, and the first outlet port 130 to thereby be moved to the first column 200. Then, the sample is separated by the eluent in the first column 200.

The first column 200 is connected to the first outlet port 130 of the sample inlet valve 100 to primarily separate materials in the sample.

The first switching valve 300 adjusts materials separated in the first column 200 so as to be introduced through a second inlet port 310 and then discharged to the outside through a first drain port 301 or discharged through a second outlet port 320. In addition, the first switching valve 300 includes a mobile-phase inlet port 330 connected to a second mobile-phase pump 302 so that a diluting mobile phase is introduced therethrough, and a mobile-phase outlet port 340 through which the diluting mobile phase is discharged.

The second switching valve 400 adjusts the materials discharged to the second outlet port 320 so as to be directly moved to the mass spectrometer (MS) or discharged to a third outlet port 410.

The T shaped connector tube 500 is a 'T'-letter shaped tube including a first port 510 connected to the mobile-phase outlet port 340 of the first switching valve 300, a second port 520 connected to the third outlet port 410 of the second switching valve 400, and a third port 530 in which fluids introduced through the first port 510 and the second port 520 are mixed with each other to thereby flow.

The second column 600 is connected to the third port 530, secondarily separates predetermined materials in the sample, and connected to the second switching valve 400 so that the separated material is moved to the mass spectrometer (MS) through the second switching valve 400.

Particularly, the first switching valve 300 may change a flow path by a switching operation so that the materials separated in the first column 200 are moved to the second switching valve 400, but adjust whether the diluting mobile phase supplied from the second mobile-phase pump 302 passes through the second switching valve 400 to flow to the second port 520 of the T shaped connector tube 500 or is directly connected to the first port 510 through the mobile-phase outlet port 340.

In addition, as described above, the first switching valve 300 may allow materials separated in the first column 200 to be discharged to the outside through the first drain port 301.

Further, the second switching valve 400 may change a flow path by a switching operation so that among the materials separated in the first column 200, only a predetermined material passes through the second column 600, but adjust whether the diluting mobile phase supplied from the second mobile-phase pump 302 passes through the second column 600 to flow to the mass spectrometer (MS) or passes through the second column 600 to thereby be discharged to the outside through the second drain port 401.

A two-dimensional liquid chromatography method using the above-mentioned two-dimensional liquid chromatography system 1 will be described. The two-dimensional liquid chromatography method includes: a) a first step of primarily separating a sample introduced from the sample inlet valve 100 in the first column 200 and introducing the primarily separated sample into the mass spectrometer (MS) sequentially through the first switching valve 300 and the second switching valve 400 (S100); b) a second step of confirming elution times of materials in the sample through the first step (S100) (S200); c) a third step of discharging the other materials except for a material of interest in the sample introduced from the sample inlet valve 100 to the first drain port 301 by switching the first switching valve 300 (S300); and d) a fourth step of collecting the material of interest in the sample introduced from the sample inlet valve 100 in the second column 600 through the second switching valve 400 and the T shaped connector tube 500 by switching the first switching valve 300 (S400).

Particularly, in the two-dimensional liquid chromatography method according to the present invention, the second column 600 is not affected by an eluate of the first column 200 by allowing the diluting mobile phase to be discharged to the mobile-phase outlet port 340 and introduced to the first port 510 of the T shaped connector tube 500 and allowing the sample introduced into the second port 520 to reach the second column 600 in a state in which the sample is diluted to a predetermined concentration in the fourth step (S400), such that at the time of separating a matrix eluted simultaneously with the material of interest from the first column 200 into the second column 600, the matrix is separated at the same start point.

That is, according to the present invention, when the material of interest and the matrix to be separated in the second column 600 are collected at a separation start point of the second column 600, the material of interest and the matrix are diluted by flowing a suitable diluting mobile phase so as to prevent separation efficiency from being decreased due to the material of interest and the matrix which are not collected to one portion but diffused by an organic solvent in the case of a reversed-phase chromatography method and by water in the case of a normal-phase chromatography method.

Further, the two-dimensional liquid chromatography method according to the present invention may further include, after performing the fourth step (S400) for a predetermined time, a fifth step of discharging all unnecessary materials eluted from the first column 200 by switching the first switching valve 300 to the first drain port 301 or introducing the diluting mobile phase into the mass spectrometer (MS) through the second column 600 after stopping a flow of the eluent in the first mobile-phase pump 302 and introducing the diluting mobile phase to the second port 520 of the T shaped connector tube 500 through the first switching valve 300 and the second switching valve 400 (S500).

For convenience of explanation, hereinafter, the two-dimensional liquid chromatography method according to the present invention will be described based on the case of performing secondary analysis on a third material in the sample in which three materials are detected by way of example supposing that each of those materials is co-eluted with matrix in the first column.

Figure 3:
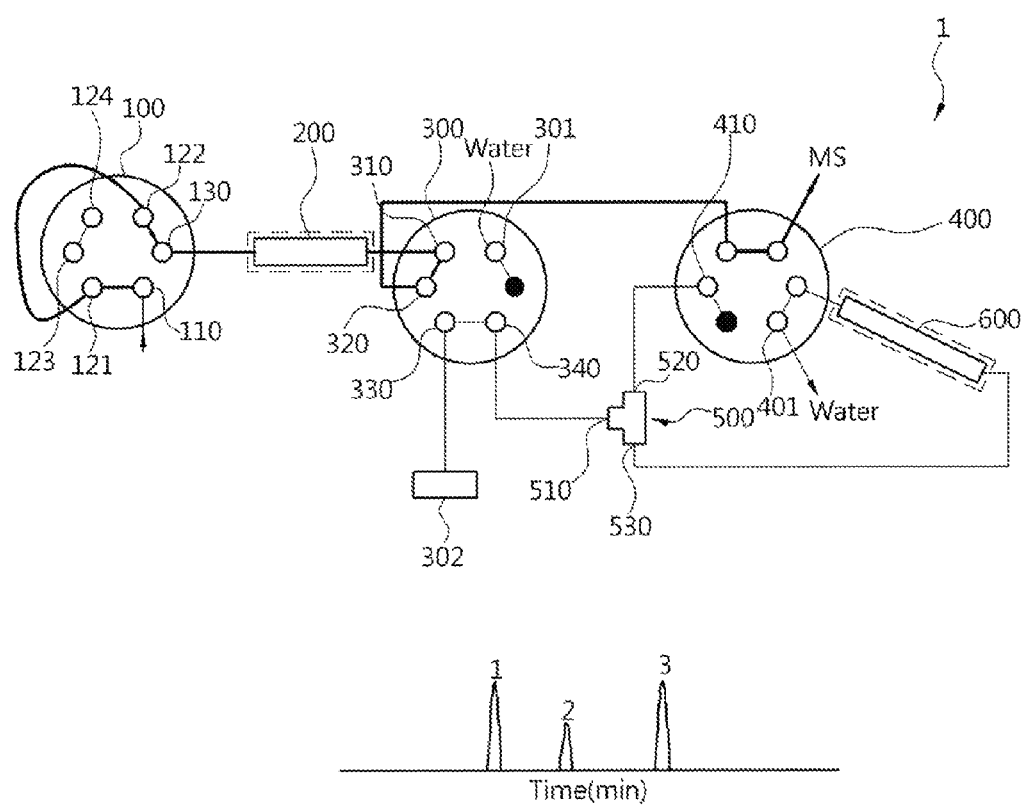
FIGS. 3 to 6 are sample flow charts illustrating each process of analyzing a sample in the two-dimensional liquid chromatography system of FIG. 2.

First, as illustrated in FIG. 3, the sample introduced through the first inlet port 110 of the sample inlet valve 100 is primarily separated in the first column 200 through the first outlet port 130.

Thereafter, the separated sample is introduced through the second inlet port 310 of the first switching valve 300, moved to the second switching valve 400 through the second outlet port 320, and then, moved to the mass spectrometer (MS) (first step (S100)).

At this time, analysis is performed in the mass spectrometer (MS) so as to confirm elution times of materials of the sample separated in the first column 200 (second step (S200)).

Figure 4:
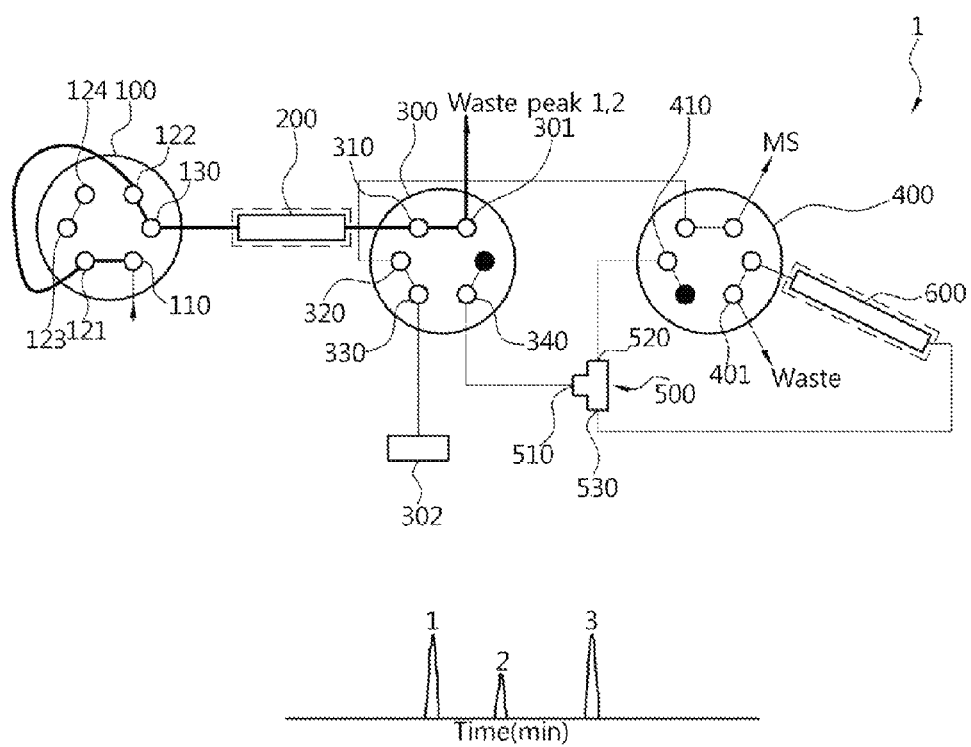

Next, the same sample is newly injected, such that each material in the sample is separated in the first column 200. In this case, during the detected elution times of first and second materials, the first and second materials separated in the first column 200 are discharged to the first drain port 301 by switching the first switching valve 300 (third step (S300), see FIG. 4).

Then, after the elution time of the second material goes on, at the time at which a third material is eluted, the first switching valve 300 is switched again, such that the third material separated in the first column 200 is introduced into the second switching valve, discharged to the third outlet port 410, and introduced to the second port 520 of the T shaped connector tube 500.

Figure 5:
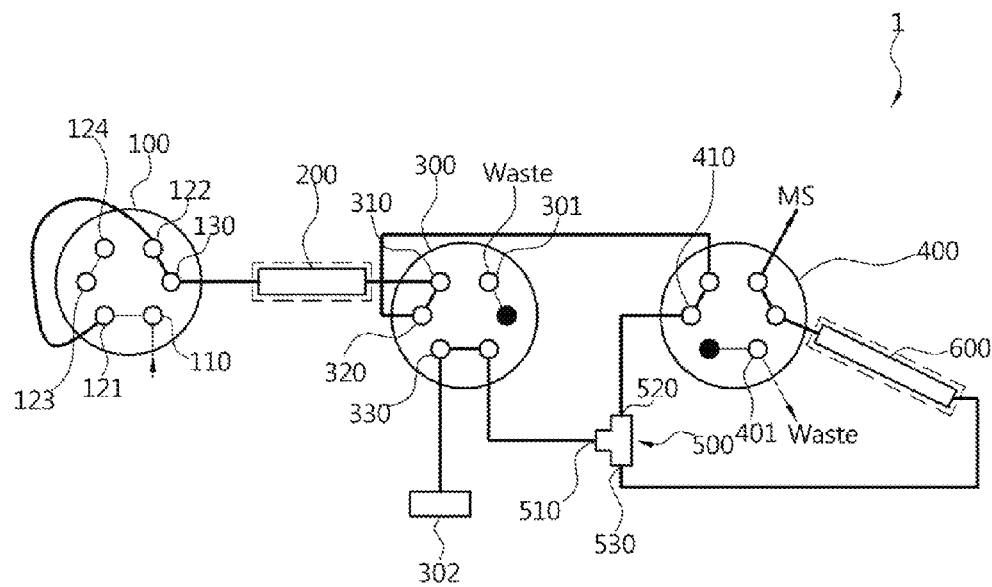

In this case, the first switching valve 300 allows the diluting mobile phase connected to the second mobile-phase pump 302 to be introduced into the first port 510 through the mobile-phase outlet port 340 and allows the sample introduced into the second port 520 to reach the second column 600 in a state in which the sample is diluted to a predetermined concentration, thereby allowing the third material, which is of interest, to be collected (fourth step (S400), see FIG. 5).

Next, after performing the fourth step (S400) for a predetermined time, all materials eluted from the first column 200 are discharged to the first drain port 301 or a flow of the mobile-phase is stopped by switching the first switching valve 300.

Figure 6:
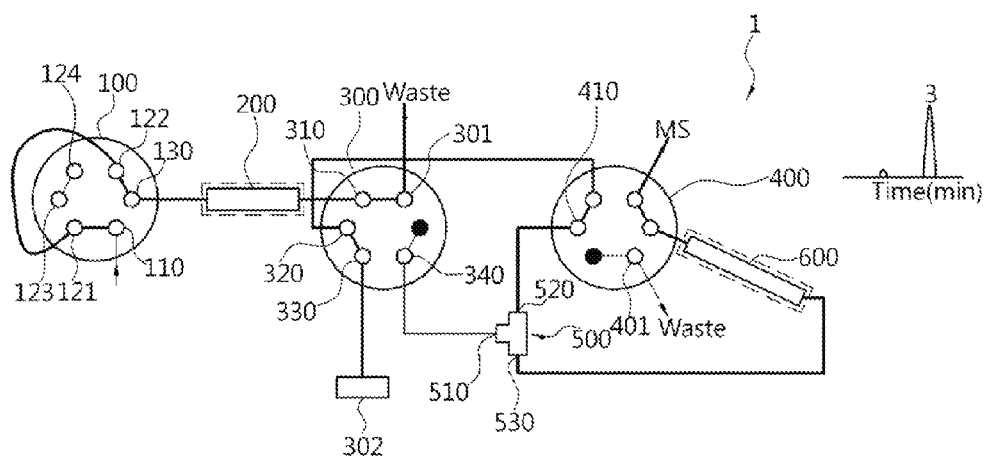

In this case, the eluate discharged from the second mobile-phase pump 302 for material separation is introduced through the mobile-phase inlet port 330 of the first switching valve 300, discharged to the third outlet port 410 through the second switching valve 400, introduced into the second port 520 of the T shaped connector tube 500, and then introduced into the mass spectrometer (MS) through the second column 600, such that the third material collected in the fourth step (S400) and the matrix having the same elution time as that of the third material are re-separated in the second column 600 (fifth step (S500), see FIG. 6).

Therefore, the two-dimensional liquid chromatography system 1 according to the present invention is formed so that both independent one-dimensional separation through the reversed-phase or normal-phase chromatography method and the two-dimensional separation for removing the matrix effect may be performed in the single system, and among the materials separated in the first column, the material of interest is re-separated in the second column, but the material of interest and the matrix are re-separated in a state in which an influence of the organic solvent or water is minimized by diluting the material of interest so as to be stably collected in the second column, thereby making it possible to improve efficiency and accuracy of the material analysis.

Further, according to the present invention, since in the case of applying the heart-cut method, it is possible to detect accurate information on the elution times of the materials separated in the first column, accuracy in collecting and re-separating the material of interest in the second column may be increased.

The two-dimensional liquid chromatography system according to the present invention has an advantage that both independent one-dimensional separation through the reversed-phase or normal-phase chromatography method and two-dimensional separation for removing the matrix effect may be performed in the single system.

In other words, the two-dimensional liquid chromatography system according to the present invention is configured so that among the materials separated in the first column, the material of interest may be re-separated in the second column, but since it is possible to detect accurate information on the elution times of the materials separated in the first column, separation accuracy in collecting and re-separating the material of interest in the second column may be increased.

Further, during a process in which the material of interest separated in the first column is eluted together with the eluent such as water or the organic solvent to thereby be collected in the second column, a problem in collection stability may be caused by the eluent. In order to solve this problem, according to the present invention, the influence by the eluent supplied from the first mobile-phase pump may be minimized by diluting the material of interest so as to be stably collected in the second column, and thereafter, the matrix having the same elution time as that of the material of interest in the first column is removed by re-separation of the material using the second column, thereby making it possible to improve efficiency and accuracy of material analysis.

In addition, according to the present invention, the flows of all liquids flowing through the second column may be induced to the mass spectrometer while the material of interest in the sample is collected, such that it is possible to confirm whether or not the material of interest is lost, and thus, it is possible to try to optimize collecting conditions, such that the entire system may be easily controlled.

The present invention is not limited to the above-mentioned exemplary embodiments but may be variously applied, and may be variously modified by those skilled in the art to which the present invention pertains without departing from the gist of the present invention claimed in the claims.

What is claimed is:

1. A two-dimensional a reversed-phase or normal-phase two-dimensional liquid chromatography system, comprising:
   a first column primarily separating materials in an injected sample;
   a first switching valve adjusting the materials separated in the first column so as to be introduced through a second inlet port and then discharged to the outside through a first drain port or discharged through a second outlet port and including a mobile-phase inlet port connected to a second mobile-phase pump so that a diluting mobile phase is introduced therethrough, and a mobile-phase outlet port through which the diluting mobile phase is discharged;
   a second switching valve adjusting the materials discharged to the second outlet port so as to be directly moved to a mass spectrometer (MS) or discharged to a third outlet port;
   a T-shaped connector tube including a first port connected to the mobile-phase outlet port of the first switching valve, a second port connected to the third outlet port of the second switching valve, and a third port in which fluids introduced through the first port and the second port are mixed with each other to thereby flow; and
   a second column connected to the third port, secondarily separating a predetermined material in the sample, and connected to the second switching valve so that the separated material is moved to the MS through the second switching valve;
   wherein the first switching valve and the second switching valve are configured to be switched so that among materials separated in the first column, only a material of interest is selectively re-separated in the second column, but the material of interest reaching the second column is diluted by the diluting mobile phase supplied through the second mobile-phase pump connected to the first switching valve to thereby be analyzed in the MS.

2. The two-dimensional liquid chromatography system of claim 1, wherein the first switching valve changes a flow path by a switching operation so that the materials separated in the first column are moved to the second switching valve, but adjusts whether the diluting mobile phase or an eluent supplied from the second mobile-phase pump passes through the second switching valve to flow to the second port of the T-shaped connector tube or is directly connected to the first port through the mobile-phase outlet port.

3. The two-dimensional liquid chromatography system of claim 2, wherein the second switching valve changes a flow path by a switching operation so that among the materials separated in the first column, only a predetermined material passes through the second column, but adjusts whether the diluting mobile phase or the eluent supplied from the second mobile-phase pump passes through the second column to flow to the MS or passes through the second column to thereby be discharged to the outside through a second drain port.

4. A two-dimensional liquid chromatography method using the two-dimensional liquid chromatography system of claim 1, the two-dimensional liquid chromatography method comprising:
   a) a first step of primarily separating the injected sample in the first column and introducing the primarily separated sample into the MS sequentially through the first switching valve and the second switching valve;
   b) a second step of detecting elution times of materials in the sample through the first step;
   c) a third step of discharging other materials except for the material of interest among the materials separated in the first column to the first drain port by switching the first switching valve; and
   d) a fourth step of collecting the material of interest among the materials separated in the first column in the second column through the second switching valve and the T-shaped connector tube by switching the first switching valve.

5. The two-dimensional liquid chromatography method of claim 4, wherein, in the fourth step,
   the diluting mobile phase is discharged to the mobile-phase outlet port to thereby be introduced into the first port of the T-shaped connector tube, and
   the sample introduced into the second port reaches the second column in a state in which the sample is mixed with the diluting mobile phase to thereby be diluted to a predetermined concentration.

6. The two-dimensional liquid chromatography method of claim 5, further comprising, after performing the fourth step for a predetermined time, a fifth step of discharging the other materials except for the material of interest among the materials separated in the first column to the first drain port and introducing the material of interest into the second port of the T-shaped connector tube through the first switching valve and the second switching valve to collect the material of interest in one end of the second column together with the diluting mobile phase supplied from the second mobile-phase pump by switching the first switching valve, and
   introducing the material of interest into the MS through an eluent supplied from the second mobile-phase pump after separating the material of interest in the second column.

* * * * *